(12) United States Patent
Smith et al.

(10) Patent No.: US 8,010,181 B2
(45) Date of Patent: Aug. 30, 2011

(54) SYSTEM UTILIZING RADIO FREQUENCY SIGNALS FOR TRACKING AND IMPROVING NAVIGATION OF SLENDER INSTRUMENTS DURING INSERTION IN THE BODY

(75) Inventors: David W. Smith, Scottsdale, AZ (US); Regina DeSanctis-Smith, Scottsdale, AZ (US); Alan M. Pitt, Phoenix, AZ (US); Nicholas Theodore, Phoenix, AZ (US); Neil Crawford, Tempe, AZ (US)

(73) Assignee: Catholic Healthcare West, Phoenix, AZ (US)

( * ) Notice: Subject to any disclaimer, the term of this patent is extended or adjusted under 35 U.S.C. 154(b) by 408 days.

(21) Appl. No.: 11/676,023

(22) Filed: Feb. 16, 2007

(65) Prior Publication Data
US 2007/0238985 A1   Oct. 11, 2007

Related U.S. Application Data

(60) Provisional application No. 60/775,816, filed on Feb. 16, 2006, provisional application No. 60/774,586, filed on Feb. 16, 2006.

(51) Int. Cl.
*A61B 5/05* (2006.01)
(52) U.S. Cl. .......................... 600/424; 600/411; 600/427
(58) Field of Classification Search ........................ None
See application file for complete search history.

(56) References Cited

U.S. PATENT DOCUMENTS

| | | | |
|---|---|---|---|
| 4,799,062 A | 1/1989 | Sanderford, Jr. et al. | |
| 4,931,047 A | 6/1990 | Broadwin et al. | |
| 5,377,678 A | 1/1995 | Dumoulin et al. | |
| 5,445,150 A | 8/1995 | Dumoulin et al. | |
| 5,808,665 A * | 9/1998 | Green | 348/65 |
| 6,246,898 B1 | 6/2001 | Vesely et al. | |
| 6,251,110 B1 | 6/2001 | Wampler | |
| 6,272,370 B1 | 8/2001 | Gillies et al. | |
| 6,285,902 B1 | 9/2001 | Kienzle, III et al. | |
| 6,377,839 B1 | 4/2002 | Kalfas et al. | |
| 6,400,980 B1 * | 6/2002 | Lemelson | 600/478 |

(Continued)

FOREIGN PATENT DOCUMENTS

EP   1 504 713 A1   2/2005

(Continued)

OTHER PUBLICATIONS

Bone Registration Method for Robot Assisted Surgery: Pedicle Screw Insertion; K Abdel-Malek et al; *Proc Instn Mech Engrs*, vol. 211 Part H; H04895, IMechE 1997, pp. 221-233.

(Continued)

*Primary Examiner* — Long V Le
*Assistant Examiner* — Angela M Hoffa
(74) *Attorney, Agent, or Firm* — Ballard Spahr LLP

(57) ABSTRACT

The present invention concerns a system for utilizing radio frequency signals to dynamically determine the location of a medical device throughout a procedure and to improve navigation of the medical device. For these purposes, a plurality of RF receivers are mounted at operative locations in the operating room and operate on the same clock signal. The system also utilizes a diagnostic medical image such as an MRI, and overlays the position feedback signal on the image. This allows, for example, a surgeon to pick a desired spot on the diagnostic image, and then cause a robotic arm driven device to be moved to that particular spot inside the human body.

15 Claims, 4 Drawing Sheets

U.S. PATENT DOCUMENTS

| | | |
|---|---|---|
| 6,628,894 B2 | 9/2003 | Winter et al. |
| 6,675,810 B2 | 1/2004 | Krag et al. |
| 6,697,664 B2 | 2/2004 | Kienzle, III et al. |
| 6,701,176 B1 | 3/2004 | Halperin et al. |
| 6,738,656 B1 | 5/2004 | Ferre et al. |
| 6,782,285 B2 | 8/2004 | Birkenbach et al. |
| 6,833,814 B2 | 12/2004 | Gilboa et al. |
| 6,837,892 B2 | 1/2005 | Shoham et al. |
| 7,015,859 B2 | 3/2006 | Anderson |
| 7,164,968 B2 | 1/2007 | Treat et al. |
| 2003/0060702 A1 | 3/2003 | Kuth et al. |
| 2003/0192557 A1 | 10/2003 | Krag et al. |
| 2004/0097806 A1* | 5/2004 | Hunter et al. ........... 600/434 |
| 2004/0138555 A1 | 7/2004 | Krag et al. |
| 2004/0171924 A1* | 9/2004 | Mire et al. ........... 600/407 |
| 2004/0172044 A1 | 9/2004 | Grimm et al. |
| 2005/0096502 A1 | 5/2005 | Khalili |
| 2005/0113659 A1 | 5/2005 | Pothier et al. |
| 2005/0148856 A1 | 7/2005 | Schulze et al. |
| 2005/0154376 A1 | 7/2005 | Riviere et al. |
| 2005/0203382 A1* | 9/2005 | Govari et al. ........... 600/424 |
| 2005/0222554 A1 | 10/2005 | Wallace et al. |
| 2005/0240125 A1* | 10/2005 | Makin et al. ........... 601/2 |
| 2005/0261591 A1* | 11/2005 | Boctor et al. ........... 600/462 |
| 2006/0098851 A1 | 5/2006 | Shoham et al. |
| 2006/0111704 A1* | 5/2006 | Brenneman et al. ........... 606/41 |
| 2006/0200026 A1* | 9/2006 | Wallace et al. ........... 600/424 |
| 2006/0241588 A1* | 10/2006 | Heim et al. ........... 606/48 |
| 2007/0021738 A1* | 1/2007 | Hasser et al. ........... 606/1 |
| 2007/0113860 A1 | 5/2007 | Anderson |
| 2007/0123748 A1 | 5/2007 | Meglan |
| 2007/0129633 A1* | 6/2007 | Lee et al. ........... 600/439 |
| 2007/0135803 A1 | 6/2007 | Belson |
| 2007/0197896 A1* | 8/2007 | Moll et al. ........... 600/407 |
| 2008/0154389 A1* | 6/2008 | Smith et al. ........... 700/24 |
| 2008/0215181 A1* | 9/2008 | Smith et al. ........... 700/245 |
| 2008/0294285 A1 | 11/2008 | Shoham et al. |

FOREIGN PATENT DOCUMENTS

| | | |
|---|---|---|
| WO | WO2005/111942 A1 | 11/2005 |

OTHER PUBLICATIONS

Image-Guided Robotic Radiosurgery [Concepts and Innovations]; John R. Adler, Jr., MD et al; *Neurosurgery*, vol. 44(6), Jun. 1999, pp. 1299-1306.

Percutaneous Spinal Interventions; Arun Paul Amar, MD et al; *Neurosurg Clin N Am*, vol. 16, 2005, pp. 561-568.

Robotically Assisted Perventricular Closure Of Perimembranous Ventricular Septal Defects: Preliminary Results in Yucatan Pigs; Zahid Amin, MD et al; *The Journal of Thoracic and Cardiovascular Surgery*, vol. 131, No. 2, Feb. 2006, pp. 427-432.

Primary And Revision Total Hip Replacement Using The Robodoc System; William L. Bargar, MD et al; *Clinical Orthopaedics And Related Research*, No. 354, Sep. 1998, pp. 82-91.

Charite Campus Virchow-Klinikum; Professor Dr. Mult et al; *Clinic for Maxillofacial Surgery-Clinical Navigation and Robotics*, Mar. 2004, p. 1389.

A Faster Method For 3D/2D Medical Image Registration—A Simulation Study; Wolfgang Birkfellner et al; *Phys. Med. Biol.*, vol. 48, 2003, pp. 2665-2679.

State Of The Art In Surgical Robotics: Clinical Applications And Technology Challenges; Kevin Cleary, PhD et al; *Computer Aided Surgery*, vol. 6, 2001, pp. 312-328.

Technology Improvements For Image-Guided And Minimally Invasive Spine Procedures; Kevin Cleary et al; *IEEE Transactions On Information Technology in Biomedicine*, vol. 6, No. 4, Dec. 2002, pp. 249-261.

Interventional Robotics Systems: Applications And Technology State-Of-The-Art; Kevin Cleary et al; *Minimally Invasive Therapy*, vol. 15:2, 2006, pp. 101-113.

A Review Of Robotics In Surgery; B. Davies; *Proc Instn Mech Engrs*; vol. 214, Part H, 1999, pp. 129-140.

Active Compliance In Robotic Surgery—The Use Of Force Control As a Dynamic Constraint; B.L. Davies et al; *Proc Instn Mech Engrs*, vol. 211, Part H, pp. 285-292, 1997.

Minimally Invasive Procedures For Disorders Of The Lumbar Spine; H. Gordon Deen, MD et al; *Mayo Clin Proc.*, vol. 78, Oct. 2003, pp. 1249-1256.

3D-2D Projective Registration Of Free-Form Curves And Surfaces; Jacques Feldmar et al; *Computer Vision And Image Understanding*, vol. 65, No. 3, Mar. 1997, pp. 403-424.

System For Robotically Assisted Prostate Biopsy And Therapy With Intraoperative CT Guidance; Gabor Fichtinger, PhD et al; *Acad Radiol*, vol. 9, 2002, pp. 60-74.

An Automatic Registration Method For Frameless Stereotaxy, Image Guided Surgery, And Enhanced Reality Visualization; W.E.L. Grimson et al; *IEEE Transactions On Medical Imaging*, vol. 15, No. 2, Apr. 1996, pp. 129-140.

Clinical Paper: Comparison Of Fit And Fill Between Anatomic Stem And Straight Tapered Stem Using Virtual Implantation On The ORTHODOC Workstation; Keiji Haraguchi et al; *Computer Aided Surgery*, vol. 6, 2001, pp. 290-296.

Surface-Based Registration Of CT Images To Physical Space For Image-Guided Surgery Of The Spine: A Sensitive Study; Jeannette L. Herring et al; *IEEE Transactions On Medical Imaging*, vol. 17, No. 5, Oct. 1998, pp. 743-752.

Automatic Lumbar Vertebral Identification Using Surface-Based Registration; Jeannette L. Herring et al; *Journal Of Biomedical Informatics*, vol. 34, 2001, pp. 74-84.

An Ultrasound-Driven Needle-Insertion Robot For Percutaneous Cholecystostomy; J.Hong et al; *Phys. Med. Biol.*, vol. 49, 2004, pp. 441-455.

Comparison Of Robotic-Assisted And Manual Implantation Of a Primary Total Hip Replacement. A Prospective Study; Matthias Honl, MD et al; *The Journal Of Bone & Joint Surgery*, vol. 85-A, No. 8, Aug. 2003, p. 1470-1478.

Robotics For Surgery; Robert D. Howe et al; *Annu. Rev. Biomed. Eng.*, vol. 01, 1999, p. 211-240.

The First Clinical Application of a "Hands-On" Robotic Knee Surgery System; M. Jakopec, PhD et al; *Computer Aided Surgery*, vol. 6, 2001, pp. 329-339.

Fluoroscopic Frameless Stereotaxy For Transsphenoidal Surgery; John A. Jane, Jr., MD et al; *Neuorosurgery*, vol. 48, No. 6, Jun. 2001, p. 1302-1308.

Minimally Invasive Percutaneous Posterior Lumbar Interbody Fusion; Larry T. Khoo, MD et al; *Neurosurgery*, website of www.neurosurgery-online.com, vol. 51, Supplement 2, Nov. 2002, p. 166-181.

Development And First Patient Trial Of a Surgical Robot For Complex Trajectory Milling; Werner Korb, M.Sc., et al; *Computer Aided Surgery*, vol. 8, 2003, pp. 247-256.

Revision Surgery Of The Lumbar Spine: Anterior Lumbar Interbody Fusion Followed By Percutaneous Pedicle Screw Fixation; Sang-Ho Lee, M.D., Ph.D., et al; *J. Neurosurg: Spine*, vol. 5, Sep. 2006, pp. 228-233.

Implementation Of An Electromagnetic Tracking System For Accurate Intrahepatic Puncture Needle Guidance: Accuracy Results In An Vitro Model; Elliot B. Levy, MD, et al; *Academic Radiology*, vol. 14, No. 3, Mar. 2007, pp. 344-354.

Robotic Virtual Endoscopy: Development Of a Multidirectional Rigid Endoscope; Michael L. Levy, M.D., Ph.D., et al; *Operative Neurosurgery 1*, vol. 59, Jul. 2006, pp. 134-141.

The Application Accuracy Of The NeuroMate Robot—A Quantitative Comparison With Frameless And Frame-Based Surgical Localization Systems; Qing Hang Li, M.D., Ph.D, et al; *Computer Aided Surgery*, vol. 7, 2002, pp. 90-98.

Bone-Mounted Miniature Robotic Guidance For Pedicle Screw And Translaminar Facet Screw Placement: Part I-Technical Development And a Test Case Result; Isador H. Lieberman, M.D., et al; *Neurosurgery*, vol. 59, No. 3, Sep. 2006, pp. 641-650.

Percutaneous CT-Guided Biopsy Of Osseous Lesion Of The Spine In Patients With Known Or Suspected Malignancy; Eric Lis et al; *AJNR Am J Neuroradiol*, vol. 25, Oct. 2004, pp. 1583-1588.

Cervival Pedicle Screws: Comparative Accuracy Of Two Insertion Techniques; Steven C. Ludwig, MD, et al; *SPINE*, vol. 25, No. 20, 2000, pp. 2675-2681.

Placement Of Pedicle Screws In The Human Cadaveric Cervical Spine: Comparative Accuracy Of Three Techniques; Steven C. Ludwig, MD, et al; *SPINE*, vol. 25, No. 13, 2000, pp. 1655-1667.

Optimization Of a Spherical Mechanism For a Minimally Invasive Surgical Robot: Theoretical And Experimental Approaches; Mitchell J. H. Lum, et al; *IEEE Transactions On Biomedical Engineering*, vol. 53, No. 7, Jul. 2006, pp. 1440-1445.

Hybrid Analysis Of a Spherical Mechanism For a Minimally Invasive Surgical (MIS) Robot-Design Concepts For Multiple Optimizations; Mitchell J. H. Lum, et al; *Studies In Health Technology And Informatics*, vol. 119, 2006, pp. 349-354.

System For Robotically Assisted Percutaneous Procedures With Computed Tomography Guidance; Ken Masamune, PhD, et al; *Computer Aided Surgery*, vol. 6, 2001, pp. 370-383.

Pedicle Screw Placement Using Image Guided Techniques; P. Merloz, MD, et al; *Clinical Orthopaedics And Related Research*, No. 354, Sep. 1998, pp. 39-48.

Three-Dimensional Relation Of Skin Markers To Lumbar Vertebrae Of Healthy Subjects In Different Postures Measured By Open MRI; Falk Mörl et al; *Eur Spine J*, vol. 15, 2006, pp. 742-751.

Three-Dimensional Image Registration Of Phantom Vertebrae For Image-Guided Surgery: A Preliminary Study; Diane M. Muratore, PhD., et al; *Computer Aided Surgery*, vol. 7, 2002, pp. 342-352.

Application Of Robotics In General Surgery: Initial Experience; Ninh T. Nguyen, M.D., et al; *The American Surgeon*, vol. 70, No. 10, Oct. 2004, pp. 914-917.

Article From Internet; Website of National Institute Of Biomedical Imaging And Bioengineering; *Adding Feeling To Robot-Assisted Surgery*; Jan. 29, 2007.

Clinical Accuracy Evaluation Of Femoral Canal Preparation Using The ROBODOC System; Shunsaku Nishihara, et al; *J Orthop Sci*, vol. 9, 2004, pp. 452-461.

Force Modeling For Needle Insertion Into Soft Tissue; Allison M. Okamura, et al; *IEEE Transactions On Biomedical Engineering*, vol. 51, No. 10, Oct. 2004, pp. 1707-1716.

Development Of The Needle Insertion Robot For Percutaneous Vertebroplasty; S. Onogi et al; *Medical Image Computing And Computer-Assisted Intervention: Miccai . . . International Conference On Medical Image Computing And Computer-Assisted Intervention*, vol. 8, 2005, pp. 105-113.

Today's State Of The Art In Surgical Robotics; Peter P. Pott, et al; *Computer Aided Surgery*, vol. 10, No. 2, 2005, pp. 101-132.

Chapter 11. Radiofrequency Radiation Safety Standards; John C. Mitchell; *Radiofrequency Radiation Dosimetry Handbook, Fourth Edition*, Jun. 24, 1997.

Cervical Pedicle Screws: Conventional Versus Computer-Assisted Placement Of Cannulated Screws; Marcus Richter, MD, PhD et al; *SPINE*, vol. 30, No. 20, 2005, pp. 2280-2287.

Spherical Mechanism Analysis Of a Surgical Robot For Minimally Invasive Surgery—Analytical And Experimental Approaches; Jacob Rosen, PhD, et al; *Studies In Health Technology And Informatics*, vol. 111, 2005, pp. 422-428.

A Stereotactic/Robotic System For Pedicle Screw Placement; Julio J. Santos-Munnè et al; *Interactive Technology And The New Paradigm For Healthcare*, 1995, pp. 326-333.

Percutaneous Computer-Assisted Translaminar Facet Screw: An Initial Human Cadaveric Study; Rick C. Sasso, MD, et al; *The Spine Journal*, vol. 5, 2005, pp. 515-519.

Future Trends In The Design And Application Of Surgical Robots; Richard M. Satava, MD, FACS; *Seminars In Laparascopic Surgery*, vol. 11, No. 2, Jun. 2004, pp. 129-135.

Robotic Surgery: From Past To Future—A Personal Journey; Richard M. Satava, MD, FACS; *Surg Clin N Am*, vol. 83, 2003, pp. 1491-1500.

Computer-Assisted Spine Surgery; Dietrich Schlenzka et al; *Eur Spine J*, vol. 9, Suppl 1, 2000, pp. S57-S64.

Medical Imaging And Registration In Computer Assisted Surgery; David A. Simon, PhD et al; *Clinical Orthopaedics And Related Research*, No. 354, Sep. 1998, pp. 17-27.

Computer-Assisted Orthopedic Surgery; Nobuhiko Sugano; *J Orthop Sci*, vol. 8, 2003, pp. 442-448.

Surface-Based Registration Accuracy Of CT-Based Image-Guided Spine Surgery; Yuichi Tamura et al; *Eur Spine J*, vol. 14, 2005, pp. 291-297.

A Spine Frame For Intra-Operative Fixation To Increase Accuracy In Spinal Navigation And Robotics; Ulrich-W. Thomale et al; *Computer Aided Surgery*, vol. 10(3), May 2005, pp. 151-155.

Minimally Invasive Spinal Surgery: A Historical Perspective; Issada Thongtrangan, M.D. et al; *Meurosurg Focus*, vol. 16(1), Article 13, Jan. 2004, pp. 1-10.

Image-Guided Robotic Navigation System For Neurosurgery; Ching-Shiow Tseng et al; *Journal Of Robotic Systems*, vol. 17(8), 2000, pp. 439-447.

Article From Internet; Website of www.healthcare.ucla.edu; Robotic Surgery: Moving Beyond State Of The Art; *UCLA Physician's Update*; Winter 2005.

Robotic Assisted Laparoscopic Radical Prostatectomy Versus Retropubic Radical Prostatectomy: A Prospective Assessment Of Postoperative Pain; Todd M. Webster et al; *The Journal Of Urology*, vol. 174, Sep. 2005, pp. 912-914.

Anatomic Evaluation Of Two Different Techniques For The Percutaneous Insertion Of Pedicle Screws In The Lumbar Spine; Lothar Wiesner, MD et al; *SPINE*, vol. 24, No. 15, 1999, pp. 1599-1603.

Feasibility Study Of a Mini, Bone-Attached, Robotic System For Spinal Operations: Analysis and Experiments; Alon Wolf, PhD et al; *SPINE*, vol. 29, No. 2, 2004, pp. 220-228.

Precise Robot-Assisted Guide Positioning For Distal Locking Of Intramedullary Nails; Ziv Yaniv et al; *IEEE Transactions On Medical Imaging*, vol. 24, No. 5, May 2005, pp. 624-635.

Electromagnetic Tracking For Abdominal Interventions in Computer Aided Surgery; Hui Zhang et al; *Computer Aided Surgery*, vol. 11(3), May 2006, pp. 127-136.

Control System Architecture For a Minimally Invasive Surgical Robot; Kenneth Fodero II, et al; *Studies In Health Technology And Informatics*; vol. 119, 2006, pp. 156-158.

Navigated Control—Navigated and Interactive Controlled Drilling In Spinal Surgery; Willhelm Thomale et al; Berlin Group Abstract; *2003 Curac*.

Computer-Assisted Fluoroscopic Targeting System For Pedicle Screw Insertion; William W. Choi M.D., et al, *Neurosurgery*, vol. 47(4), Oct. 2000, pp. 872-878.

Abstract from CRISP (Computer Retrieval of Information on Scientific Projects, Abstract Display; Christopher J. Hasser; *Image-Guided Minimally Invasive Robotic Surgery*, Grant No. 1R42EB004789-01, PI Title Director, *Applied Research*, 2005, pp. 1-2.

Website article from: http://www.jbstiehlmd.com/Total%20Joint%20Reconstruction/In%20The/020News.html; Surgical Navigation—The Future Of Joint Replacement Surgery; *James Stiehl*, Oct. 2003, p. 10B.

Abstract—Comparative Results Between Conventional And Computer-Assisted Pedicle Screw Installation In The Thoracic, Lumbar, And Sacral Spine; L.P. Amiot, et al.; *Spine*, vol. 25(5), 2000, pp. 606-614.

Abstract—Robot-Assisted Placement Of Craniofacial Implants; M. Klein, et al.; *Int J Oral Maxillofac Implants*, vol. 18(5), 2003, pp. 712-718.

Abstract—Development And Evaluation Of a Spine Biopsy Simulator; Medicine Meets Virtual Reality; C. Lathan, et al.; *IOS Press and Ohmsha*, 1998, pp. 375-376.

Abstract—Robodoc: Robotics: Brave New World of Surgery—or is it?; M. Menduno; *Mater Manag Health Care* vol. 8(11), 1999, pp. 20, 22, 24.

Abstract—Accuracy Of Thoracic Vertebral Body Screw Placement Using Standard Fluoroscopy, Fluoroscopic Image Guidance, And Computed Tomographic Image Guidance: A Cadaver Study; S.K. Mirza, et al; *Spine*; vol. 28(4), 2003, pp. 402-413.

Abstract—Innovations In Surgical Approach: The Marriage Of Technique, Technology, And Judgment; P. Nakaji et al.; *Clin Neurosurg*, vol. 51, 2004, pp. 177-185.

Abstract—Adaptation Of a Hexapod-Based Robotic System For Extended Endoscopic-Assisted Transsphenoidal Skull Base Surgery; CJ Nimsky et al; *Minim Invasive Neurosurg*, vol. 47(1), 2004, pp. 41-46

Abstract—Image-Guided Insertion Of Transpedicular Screws. A Laboratory Set-Up; LP Nolte et al.; *Spine*, vol. 20(4), 1995, pp. 497-500.

Abstract—A New Approach For Modelling Kinematic Dependencies For Monitoring Locations of Objects in Closed Kinematic Chains (Part 2); M. Stien et al; *Stud Health Technol Inform*, vol. 85, 2002, pp. 504-506.

Abstract—A System For Simulation And Monitoring Of Robot-Assisted And navigation-Assisted Surgical Interventions (Part 1); M. Stien et al; *Stud Health Technol Inform*, vol. 85, 2002, pp. 501-503.

Abstract—A Novel End-Effector Design For Robotics In Image-Guided Needle Procedures; D .Sun et al; *Int J Med Robot* vol. 2(1), 2006, pp. 91-97.

Abstract—Intraoperative MR At 1.5—Tesla Experience And Future Directions; G.R. Sutherland et al; *Acta Neurochir Suppl*, vol. 85, 2003, pp. 21-28.

Abstract—Robot-assisted 3D-TRUS Guided Prostate Brachytherapy:System Integration And Validation; Z. Wei et al.; *Med Phys*, vol. 31(3), 2004, pp. 539-548.

Abstract—Technologies For Guidance Of Radiofrequency Ablation In The Multimodality Interventional Suite Of The Future; B.J. Wood et al.; *J Vasc Interv Radiol*, vol. 18(1 Pt 1), 2007, pp. 9-24.

Abstract—Percutaneous Transarticular Atlantoaxial Screw Fixation Using a Cannulated Screw System And Image Guidance; W. Borm et al.; *Minim Invasive Neurosurg*, vol. 47(2), 2004, pp. 111-114.

PCT Written Opinion of the International Searching Authority PCT/US2007/062346, (6 pages), Jun. 21, 2007.

PCT International Search Report, PCT/US2007/062346, (4 pages), Mar. 7, 2007.

\* cited by examiner

SYSTEM UTILIZING RADIO FREQUENCY SIGNALS FOR TRACKING AND IMPROVING NAVIGATION OF SLENDER INSTRUMENTS DURING INSERTION IN THE BODY

CROSS REFERENCE TO RELATED APPLICATIONS

This application claims the benefit of priority from and incorporates the disclosures of Provisional Application Ser. No 60/775,816, entitled Tracking System for Providing Actual Position and Record of Surgical Instruments and/or Medical Apparatuses During Biopsy and Surgical Procedures, and filed on Feb. 16, 2006; Provisional Application Ser. No. 60/774,586, entitled System to Improve Navigation of Slender Instruments During Insertion Into The Body, and filed on Feb. 16, 2006.

BACKGROUND OF THE INVENTION

The present invention generally relates to improvements in the field of medical devices that use radio frequency (RF) signals. More particularly, the present invention concerns a medical device used in invasive procedures that uses RF signals for multiple applications, such as tracking an invasive instrument and improving the navigation of slender instruments during insertion and progression in the body.

Various issued patents disclose using electromagnetic waves with medical devices. For example, U.S. Pat. No. 5,377,678, issued on Jan. 3, 1995, discloses a tracking system to follow the position and orientation of a device with RF fields. In the abstract of this patent, it is stated that the system disclosed in the patent involves radio frequency signals emitted by an invasive device such as a catheter. The abstract also states that the invasive device has a transmit coil attached near its end and is driven by a low power RF source to produce a dipole electromagnetic field that can be detected by an array of receive coils distributed around a region of interest. The abstract further discloses that the position and orientation of the device, as determined by the tracking system, are superimposed upon independently acquired Medical Diagnostic images, thereby minimizing the radiographic exposure times. The content of this patent is incorporated by reference into this application as if fully set forth herein.

As another example, U.S. Pat. No. 5,445,150, and issued on Aug. 29, 1995, discloses an invasive system employing a radio frequency tracking system. In the abstract of this patent, it is stated that the system disclosed in the patent involves an invasive imaging system that employs a self-contained RF transmitter attached to an invasive device within a subject without physical connections to a tracking/display system and without the use of ionizing rays. The abstract further states that the radiated RF signal is received by receive coils of a tracking/display means, which calculates the location of the RF transmitter. The tracking/display means displays the medical diagnostic image on a monitor and superimposes a symbol on the image at a position corresponding to the calculated location of the RF transmitter. The content of this patent is incorporated by reference into this application as if fully set forth herein.

Another example is U.S. Pat. No. 6,377,839, which issued on Apr. 23, 2002, and which discloses a tool guide for a surgical tool. In the abstract of this patent, it is stated that "[a] subject is secured to a subject support (10). A stereotaxic wand (40) is inserted into a tool guide (60)." The abstract also states that the wand has two emitters which selectively emit wand signals which are received by three receivers, and that a trajectory and location of the wand are superimposed on a diagnostic image on a monitor. If the surgeon is satisfied with the entry point and trajectory shown on the monitor, a surgical tool is inserted into the bore while the tool guide is held along the designated trajectory and at the designated entry point. The content of this patent is incorporated by reference into this application as if fully set forth herein.

A still further example is U.S. Pat. No. 6,701,176, which issued on Mar. 2, 2004, and which is entitled "magnetic-resonance-guided imaging, electrophysiology, and ablation". In the abstract of this patent, it is stated that the system, in its preferred embodiment, provides an invasive combined electrophysiology and imaging antenna catheter, which includes an RF antenna for receiving magnetic resonance signals and diagnostic electrodes for receiving electrical potentials. The combined electrophysiology and imaging antenna catheter are used in combination with a magnetic resonance imaging scanner to guide and provide visualization during electrophysiologic diagnostic or therapeutic procedures. The content of this patent is incorporated by reference into this application as if fully set forth herein.

A further example is U.S. Pat. No. 6,738,656, which issued on May 18, 2004, and is entitled "Automatic Registration System for use with Position Tracking an Imaging System for use in Medical Applications." The abstract of this patent states it is a method of automatic registration which includes forming an image of a body part including a representation of markers fixed in a known position in space relative to a reference mount, positioning a sensing unit in a known position in space relative to the reference mount, and automatically registering the sensing unit in a space relative to the formed image based on the location of the markers in the formed image, the known location of the markers relative to the reference mount, and the known location of the sensing unit relative to the reference mount. The content of this patent is incorporated by reference into this application as if fully set forth herein.

A further example is U.S. Pat. No. 6,833,814, which issued on Dec. 21, 2004, and is entitled "Intrabody Navigation System for Medical Applications." The abstract of this invention states it is a system and method for tracking the position and orientation of a probe such as a catheter whose transverse inner dimension may be at most about two millimeters. The abstract further states that three planar antennas that at least partly overlap are used to transmit electromagnetic radiation simultaneously, with the radiation transmitted by each antenna having its own spectrum. The content of this patent is incorporated by reference into this application as if fully set forth herein.

A further example is U.S. Pat. No. 6,251,110, which issued on Jun. 26, 2001, and is entitled "Combined Radio Frequency And Ultrasonic Surgical Device". The abstract of this invention states that it is an energy-based surgical device for the application of ultrasonic energy and Radio Frequency energy. The abstract further states that the surgical device has a housing and an acoustic assembly having an electrically conductive waveguide, and the distal end of the waveguide of the acoustic assembly has an end effector for the conduction of ultrasonic energy or Radio Frequency energy. The content of this patent is incorporated by reference into this application as if fully set forth herein.

A further example is U.S. Pat. No. 4,931,047, which issued on Jun. 5, 1990, and is entitled "Method And Apparatus For Providing Enhanced Tissue Fragmentation And/Or Hemostasis". The abstract of this invention states that it is an apparatus having a vibratable tip for ultrasonically disintegrating tissue in a surgical procedure and for aspirating the disintegrated tissue and fluids away from the surgical site through an opening in the tip. The abstract further discloses that a connection to an electrosurgical unit provides for delivery of RF cutting current, RF coagulating current, or a blend thereof, to the tip so that electrosurgical procedures can be conducted separately or simultaneously with ultrasonic aspiration through the tip. The content of this patent is incorporated by reference into this application as if fully set forth herein.

There are a number of other patents that disclose tracking devices. For example, U.S. Pat. No. 7,015,859, entitled "Electromagnetic Tracking System and Method Using a Three-Coil Wireless Transmitter" and U.S. Pat. No. 6,285,902, entitled "Computer Assisted Targeting Device for Use in Orthopaedic Surgery". U.S. Pat. No. 6,628,894 discloses a hand held camera with tomographic capability. The tomographic imaging system disclosed in the patent includes a moveable detector or detectors capable of detecting gamma radiation, one or more position sensors for determining the position and angulation of the detector(s) in relation to a gamma ray emitting source, and a computational device for integrating the position and angulation of the detector(s) with information as to the energy and distribution of gamma rays detected by the detector and deriving a three dimensional representation of the source based on the integration. The content of these patents are incorporated by reference into this application as if fully set forth herein.

Minimally invasive surgical procedures are being increasingly used to deposit or extract fluids, solid materials, or miniature devices internal to the body. Probes are being used that incorporate different devices including miniature cameras or that can apply different energy forms such as radio frequency (RF) energy to treat tissue. These types of applications require that a slender medical instrument reach a small target position internal to the body of the subject and that the position of the critical part of the medical instrument is always known through medical imaging, such as fluoroscopy.

In many cases, a user needs to insert a long flexible needle (straight or curved) through the skin and deep into soft tissues for biopsy, injection, or insertion of a smaller diameter needle or wire through the needle's cannula. The path of the needle is not necessarily straight for two main reasons. The first reason that the needle's trajectory curves is that the tip of the needle is commonly beveled to make it sharp. The user inserts the needle by pushing it along its axis and the soft tissues encountered during insertion apply a component of reaction force perpendicular to the plane of the bevel. Therefore, the tip of the needle is forced to move away from the plane of the bevel.

A second reason for the needle path varying unpredictably is that tissues of different density are encountered during insertion. The needle, in general, prefers to take the path of least resistance into the tissues that are easiest to penetrate. This path may not be the desired path.

Currently, users often use beveled curved needles to reach pathology that is unreachable by a straight path. These curved needles are usually flexible and are made of shape memory alloy (e.g., nitinol) so that they can be fed through a long, straight rigid outer shaft. They then start to bend as they exit the shaft. For example, the straight outer shaft is first inserted to a desired linear depth to one side of a critical structure with the inner shape-memory curved needle pushed out to start a curved path (tracked by fluoroscopy) around the critical structure. To steer the needle, the user changes the radius of curvature by changing the amount of needle in or out of the straight shaft and the user changes the direction of the curved path by rotating the inner curved needle within the outer straight shaft. Such a procedure requires dexterity and constant fluoroscopic imaging to ensure the proper needle path.

In addition to problems with predicting the path of the needle, it sometimes becomes difficult for the user to continue to advance the needle farther after a substantial portion of the needle is within the soft tissues. This problem occurs because the force to continue to insert the needle is the sum of the force to slice through new tissue plus the frictional resistance along the shaft of the needle that is within the tissue. As the needle is inserted farther and farther, this frictional resistance increases in direct proportion to the length of the shaft within the tissue.

Therefore, it would be desirable for the user to be able to insert a needle with better predictability of its path and with less resistance to insertion.

Radio frequency scalpels are produced by various companies (e.g., Ellman International, Oceanside, N.Y.; Meyer-Haake, Wehrheim, Germany). These scalpels have advantages over standard scalpels in that they require less force to cut tissue and the tissues do not bleed much after cutting because the small blood vessels become cauterized by the radio frequency energy. However, there exists a need for radio frequency technology to be applied to a needle tip for easier penetration with less sideways deflection to ease navigation.

A common reference for selecting the appropriate energy waveforms for certain types of procedures is described in the table on the Ellman website. The physician should be able to choose the level of energy based on whether hemostasis is desired and what types of tissues are being encountered. For example, when penetrating skin and superficial muscle, a low energy would be used, but if bone or other dense tissue were encountered, the energy could be increased.

Heretofore, the positions of surgical instruments and/or apparatuses being used during minimally invasive surgical procedures have often been tracked by taking multiple x-ray images (fluoroscopy). This method of tracking position adds time to surgical procedures, provides only discrete steps of position change, and increases the exposure to radiation energy to the subject and medical staff.

Present technology that is useful in some aspects of minimally invasive surgery is a guidance system that assists in locating the initial position of the surgical instrument and/or apparatus while it is external to the subject's body and can track rigid extensions of the instrument/apparatus that penetrate into the body. These existing guidance systems use direct line of sight and triangulation to calculate position by using two or more cameras in direct line of sight of each light source. The light sources are permanently attached to the instrument/apparatus (such as a wand) that is manually held in a spatial position relative to the subject. The position of the wand is calculated and imposed upon the diagnostic image. For tracking penetration into the subject of any kind of flexible device or of a rigid device that must penetrate deeper than the wand can allow, the position of the surgical instrument is tracked by taking multiple x-ray images. Of note, the movement of the outer surface of the subject is insufficient to account for movement of internal structures and organs. Complex internal movement can be caused by respiratory motion as well as a shift in the anatomic architecture occurring during some operative procedures (particularly partial debulking of tumor or other masses).

There are many different surgical procedures that require surgical instruments to enter the body. Many applications require that the surgery be performed using minimally invasive surgical procedures, thereby creating the minimum disturbance and damage to the tissue of the body. By using minimally invasive techniques, the risk of infection is reduced and the recovery time is shorter.

During minimally invasive surgical procedures, trying to determine the position of a surgical instrument that is internal to the body of the subject and to track the instrument's path relative to a navigation plan and to efficiently arrive at the planned target is quite cumbersome using existing technology. The efficient navigation of the surgical instrument and feedback of its precise position are critical to reducing the time and improving the quality of surgical procedures.

Therefore, there exists a need for an improvement on existing technology that tracks the precise position of a surgical device.

SUMMARY OF THE INVENTION

Accordingly, the present invention is a novel combination of using RF to perform several functions with medical equipment to correct or reduce the problems posed by current technology.

In one embodiment, the present invention relates to using RF technology for multiple applications in medical devices. The present invention provides, for example, a needle, probe, scalpel or any slender medical instrument with the RF energy at the leading edge of the instrument to reduce the mechanical forces created during penetration of tissue and/or to improve navigation of these instruments within the body in order to lessen or prevent the problems described above. This improves patient and medical staff safety and reduces the time of biopsy or minimally invasive surgical procedures. It should be noted that the RF signal emitted by the tip of the needle or guide wire be can used for different purposes depending on the stage of the procedure.

Another aspect of the present invention relates to using RF transmissions to provide dynamic feedback to track the precise three-dimensional position of surgical instruments and/or medical apparatuses being used during biopsy and minimally invasive surgical procedures. This includes dynamically tracking the surgical instrument and/or medical apparatus, overlaying its position on a diagnostic image, correcting for any deviations to the navigation path and/or correcting dynamically for any movement of the subject's body.

In one embodiment of the invention, an electrode capable of emitting RF energy is located at the tip of an invasive device. The RF energy at the tip of the device provides less resistance to insertion and reduces mechanical forces created during penetration of tissue, reducing or eliminating multiple x-ray exposures presently required to reach the target position when using biopsy needles, probes or slender medical instruments during minimally invasive surgery. Further, the RF energy reduces the need for the bevel on the tip of the needle, which is desired because a bevel creates deflecting mechanical side forces as the needle is penetrating the tissue making it difficult to reach the desired target. The RF energy is also used to correct the trajectory path of a curved biopsy needle by reducing deviation from its planned path and allowing for changing the linear and rotational relationship of the needle to the tube and angular position of the tube. As a result, accuracy and efficiency of reaching a targeted position during minimally invasive surgery is improved.

The present invention also contemplates selectively activating the RF energy at the tip of an invasive device to be used to navigate the slender medical instrument through variations in tissues using manual or automated systems.

The invention also contemplates allowing the clinician to create a controlled and accurate path from the surface of the body to the desired destination. This path can be curved, meaning that approaches that are not presently possible by a direct linear path will become possible. Examples of disease treatment using a curved path are: intervertebral disc extrusion from a contralateral posterior approach, biopsy or injection using curved path to avoid critical structures, and increased field of view during brain tumor resection through small craniotomy.

In an embodiment of the invention, a RF transmitter on the surgical instrument also emits RF signals that allows the tracking of the location of the surgical instrument.

In an embodiment, the invention provides a system for dynamically tracking three-dimensional position of surgical instruments, medical apparatuses and/or medical robotic devices being used during minimally invasive surgery. Further, the invention provides a system for precisely following a navigation path using surgical planning tools and medical images by providing the actual position of the surgical instrument and allowing the medical staff, medical robotic system (e.g., a medical instrument mounted on an end of arm tool) or medical apparatuses to make-on going corrections to continue along the navigation path. The navigation can be preplanned and/or dynamically adjusted as the procedure takes place, in order to precisely reach a targeted position within the body during minimally invasive surgical procedures.

The invention also provides a system, method and means of tracking the position of surgical instruments, medical apparatuses and or medical robotic system during surgical procedures and to continuously overlay this geometric position data onto the diagnostic images of the patient. The invention provides for increasing the positional accuracy of surgical instruments, medical apparatus and/or medical robotic system as they are used in minimally invasive surgical procedures.

In another embodiment, the invention provides a radio frequency (RF) identity to each surgical instrument so that a log of usage can be automatically recorded.

In another embodiment, a the invention provides a system where multiple probes can be inserted in internal soft tissues and then tracked in real-time to display the real-time deformation of the soft tissues.

Some of the benefits of the present invention include reducing the time and improving safety for minimally invasive surgical procedures, efficiently implanting devices, and expanding the use of minimally invasive surgical procedures. Other benefits include reducing the forces required in penetrating tissue with slender instruments and providing more predictability of movement with less resistance to insertion of slender instruments.

BRIEF DESCRIPTION OF THE DRAWINGS

Various examples objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
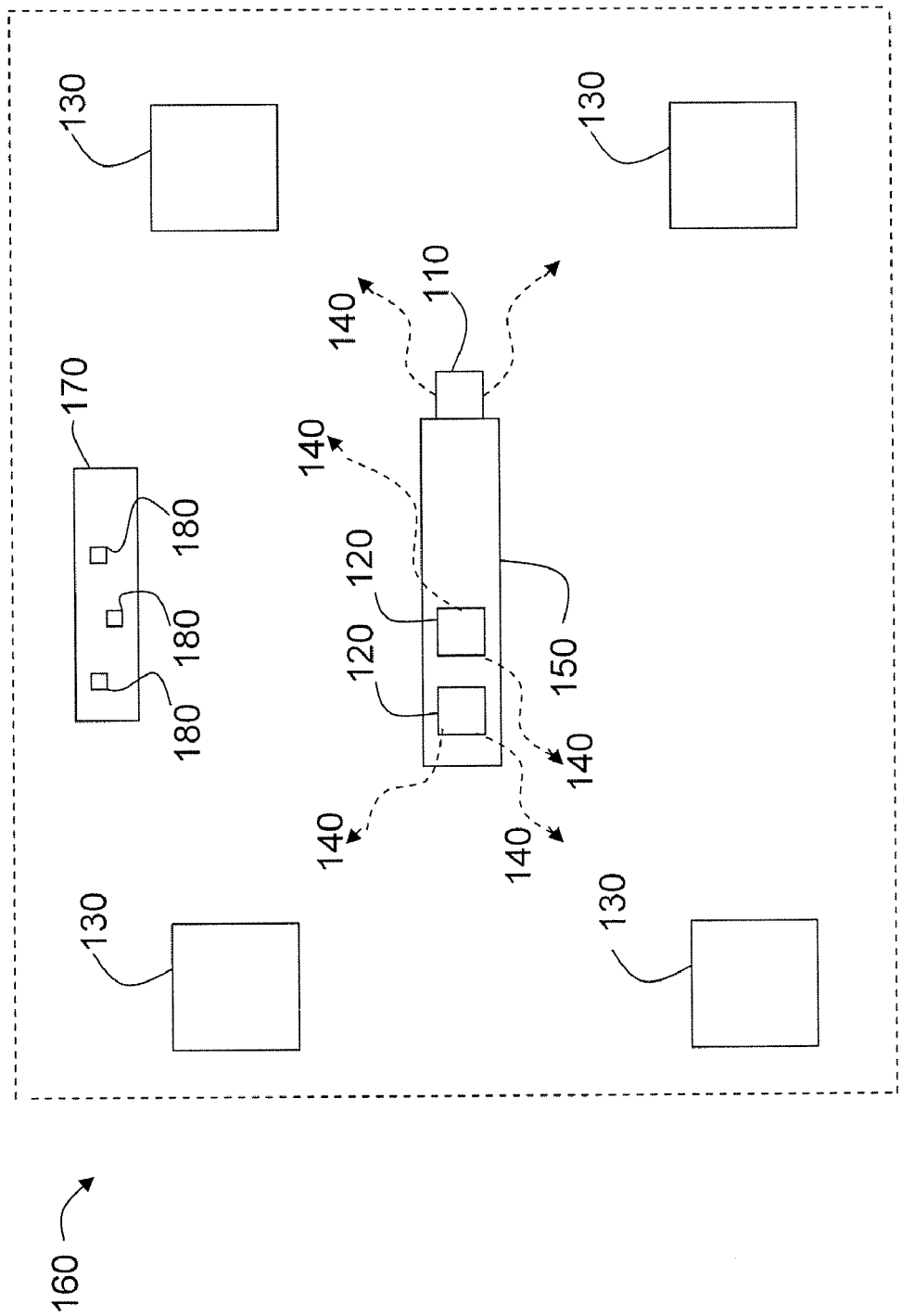
FIG. 1 is a schematic diagram of a medical device utilizing radiofrequency signals to dynamically determine the location of said medical device throughout the procedure, and also utilizing RF energy to improve navigation of said medical device according to an embodiment of the invention.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated. It should be further understood that the title of this section of this specification, namely, "Detailed Description Of The Preferred Embodiments", relates to a requirement of the United States Patent Office, and does not imply, nor should be inferred to limit the subject matter disclosed herein.

In the present disclosure, the words "a" or "an" are to be taken to include both the singular and the plural. Conversely, any reference to plural items shall, where appropriate, include the singular.

For the purpose of this description an Operating Room is any room in which surgical procedures are performed. The term surgical instrument for the purposes of this invention relates to any instrument, medical apparatus or medical robotic system used during surgical procedures.

FIG. 1 is a schematic diagram of a medical device utilizing radio frequency signals to dynamically determine the location of said medical device throughout the procedure, and also utilizing RF energy to improve navigation of said medical device, according to an embodiment of the invention. The system shown in FIG. 1 includes Local Positioning System (LPS) 160, LPS calibration device 170 and surgical instrument 150. Surgical instrument 150 includes RF transmitters 120, which transmit RF transmissions 140, and RF tip 110. RF transmitters 120 are embedded into the structure of surgical instrument 150. Alternatively, RF transmitters 120 are attached to surgical instrument 150. RF tip 110 is attached to an end of surgical instrument 150. LPS 160 includes a plurality of RF receivers 130. The LPS for the operating room can be created because the RF receivers 130 are located at known fixed positions in the operating room, the RF receivers 130 operate on the same clock signal, and also the precise location of RF receivers 130 relative to each other are known. LPS calibration device 170 includes calibration RF transmitters 180.

In certain embodiments, the RF energy emitted by RF tip 110 can be changed from a level useful for navigating through tissue to a level useful for tracking the position of the RF tip 110 in the LPS 160. This change in RF energy level can be automatic, occurring at defined temporal intervals, in reaction to sensed events, or it can be user-selected.

In operation of certain embodiments, the precise position of surgical instrument 150 is tracked during surgery using the RF transmissions 140 transmitted by RF transmitters 120 and RF tip 110. LPS 160 uses triangulation of RF transmissions 140 to determine the position. Alternatively, only a single RF transmitter 120 and/or RF tip 110 is attached to surgical instrument 150.

LPS calibration device 170 establishes and calibrates the positions of each of the RF receivers 130 relative to each other. The LPS calibration device 170 incorporates a multiple of calibration RF transmitters 180 that are positioned at known locations on the LPS calibration device 170 and that are capable of transmitting a range of frequencies and identification signals.

Alternative to a LPS calibration device 170, a precision positioning system (not shown) is used. The precision positioning system incorporates single or multiple RF transmitters capable of transmitting a range of frequencies and identification signals. Either method will use three transmitted signals to account for known points on a rigid structure to be tracked in three dimensions. All RF receivers 130 in the operating room receive the signals from the transmitters on the LPS calibration device 170 or precision positioning system where the unique relative positions of the RF receivers 130 can be calculated by triangulation.

In operation, surgical instrument 150 having multiple RF transmitters 120 imbedded into its structure will transmit signals to the RF receivers 130 in the operating room. Alternatively, surgical instrument 150 only has a single transmitter, RF tip 110 or RF transmitter 120. A single transmitter will allow the position of a key point on surgical instrument 150 to be tracked (e. g., the tip or center of mass). Two transmitters, for instance RF tip 110 and one RF transmitter 120, will allow the position and orientation of a vector to be tracked (e.g., tip and shaft orientation of a straight guide tube). Three or more transmitters will allow all points on the rigid body of surgical instrument 150 to be tracked in three dimensions (e.g., a surgical plate that is being inserted). RF transmitters 120 and RF tip 110 are imbedded in the instrument in known positions relative to surgical instrument 150's geometry. Previously recorded and stored dimensional data can be used to overlay images of surgical instrument 150 on the points whose positions are being tracked.

A battery or any other power source (not shown) can power the RF transmitters 120 and/or RF tip 110; each has a unique identity and is capable of transmitting (if required) at different frequencies. In some embodiments RF tip 110 is capable of transmitting at frequencies useful for improving the navigation of slender instruments during insertion into the body.

To track surgical instrument 150, the RF signals 140 are detected by each of the RF receivers 130 positioned in the operating room. Using triangulation calculations, the unique position of either RF transmitters 120 or RF tip 110 in the coordinate system of the operating room can be determined. This position and the position of surgical instrument 150 can then be overlaid on a representation (e.g. medical image) of the anatomy through a calibration process, which relates the coordinate location of the anatomy in the medical image to the coordinate location of the instrument in the operating room (see FIG. 2).

In an embodiment of the invention, RF transmitters (not shown) can be attached to anatomical structures (e.g., glued to skin, inserted via a needle into soft tissue) in known locations to calibrate the anatomy of a subject (not shown) relative to the coordinate system of the operating room.

To track surgical instrument 150, the RF signals 140 travel at a predictable velocity through air, and thus the position of RF transmitters 120 and RF tip 110 can be calculated with greatest accuracy before the instrument enters the subject. After the surgical instrument 150 enters the subject, the RF signal's 140 velocity may be altered due to the density of the tissue through which it travels. Accuracy of the detected transmitter position may be altered in this case if the signal experiences a delay as it travels through different tissues. Corrections and adjustments to the triangulation signals and calculations will be made based on the density of the tissues being penetrated and the approximate distance of the instrument within the tissues (based on depth and angle of instrument penetration).

In an embodiment of the present invention, RF energy in RF tip 110 is changed (if necessary) to a level for improving navigation of surgical device 150 during insertion into the body. This improvement in navigation is further explained in FIG. 4.

In an embodiment of the present invention, multiple flexible probes with RF tips are inserted into soft tissues in the body used for real-time tracking of soft tissue displacement during the insertion of an instrument. The user will insert these thin probes in the region of interest near deforming internal tissues and organs. Each probe will have a RF tip with unique identifier. The subject will then receive a CT or MRI scan after probes are inserted. Then, since the positions of the tips can be visualized on the CT or MRI scans relative to the organs and soft tissues, the exact location of the tips relative to the internal structures can be defined. Since the tip location may be tracked in real-time, the movement of internal structures in response to breathing or pressure (such as the pressure of instruments performing a procedure nearby) can be tracked in real-time.

The internal tracking information from multiple flexible probes with RF tips will be used to precisely locate the inserted instrument as it travels through moving tissue. If a tracking tip is attached to an instrument such as a flexible catheter, the position of the instrument tip is known relative to each of the thin probes, and therefore the position of the instrument tip is known relative to the moving organs and soft tissues. Computerized display can make use of known tissue deformation mechanics to portray a real-time representation of the deforming tissues (based on their original appearance from the CT or MRI) on a monitor for the user. The more probes that are used, the better the accuracy of the intervention. At least three probes are needed for determining an accurate initial position (before any deformation) to synchronize with medical images.

Figure 2:
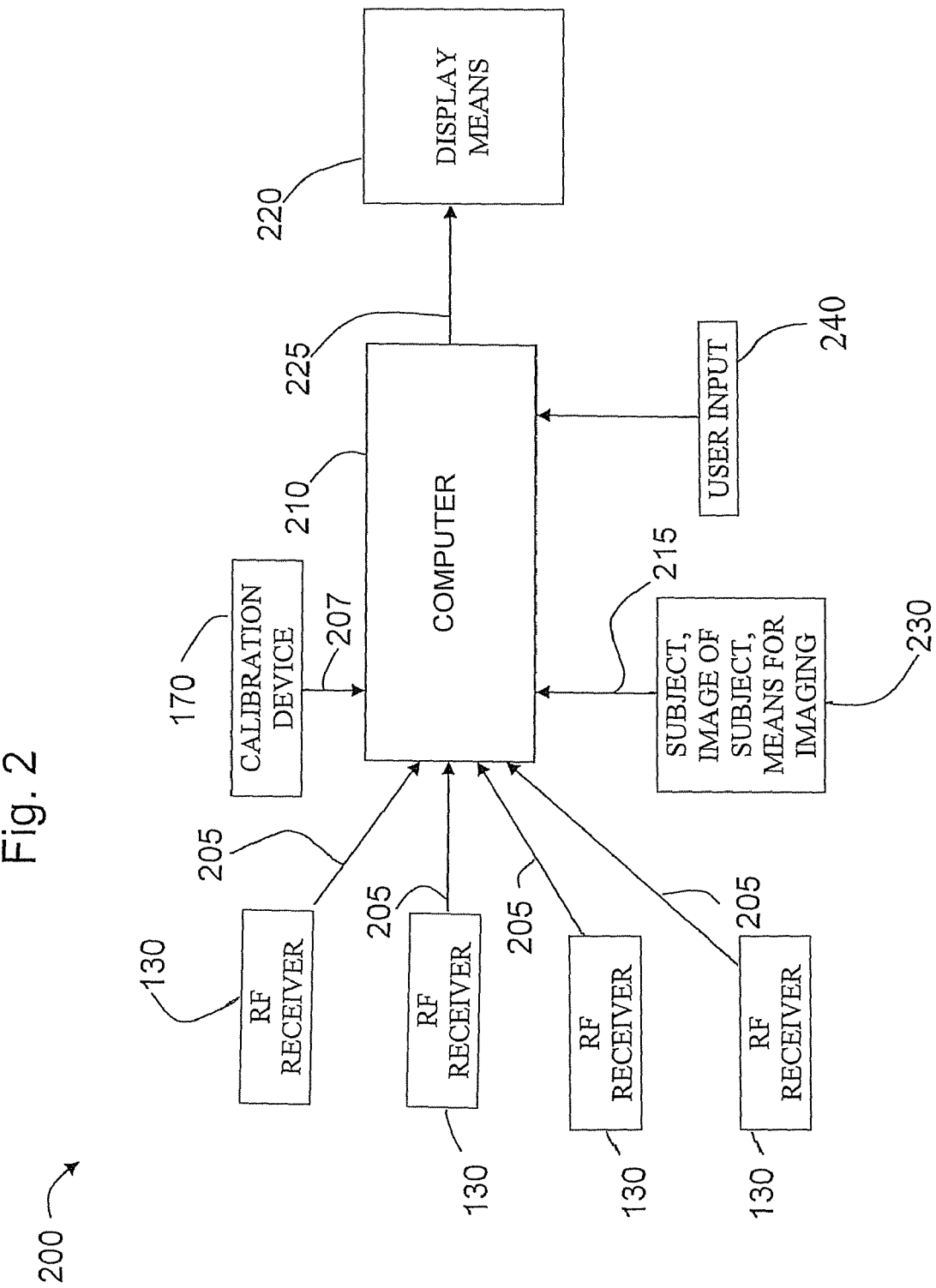
FIG. 2 is a schematic diagram of a subsystem that dynamically calculates the position of a surgical instrument and superimposes said position on an image of the subject according to an embodiment of the present invention.

FIG. 2 is a schematic diagram of a subsystem that dynamically calculates the position of a surgical instrument and superimposes said position on an image of the subject 230, according to an embodiment of the present invention. The system 200 includes a plurality of RF receivers 130, a computer 210, a means for acquiring an anatomical image of the subject 230, a user input 240, an LPS calibration device 170, and a display means 220. The RF receivers 130 are in electronic communication with computer 210 by connection 205. The LPS calibration device 170 is in electronic communication with computer 210 by connection 207. The means for acquiring an anatomical image of the subject 230 is also in electrical communication with the computer 210 by connection 215. The user may make adjustments to the system through user inputs 240, which are detected by computer 210. The computer is in electric communication with the display means 220 through connection 225.

In operation, computer 210 receives LPS calibration data from LPS calibration device 170 through connection 207. This enables computer 210 to create the LPS coordinate system of the operating room.

Then, computer 210 needs to calibrate the anatomy relative to the coordinate system of the operating room. RF receivers 130 receive RF signals from RF transmitters attached to anatomical structures (not shown). The RF receivers 130 communicate said received RF signal to computer 210 through connection 205. Computer 210 then uses this information to calibrate the anatomical position of the subject relative to the coordinate system of the room. Further, positions of these transmitters can then be tracked to account for subject movement (e.g., breathing) or organ movement (e.g., displacement of the organ away from a tool that is being inserted). The anatomical representation displayed on display means 220 can be shifted, scaled, or distorted as necessary to depict such movement. These adjustments to the anatomical representation can either be made automatically by computer 210, or be user-initiated through user input 240. Alternatively, if less accuracy is required and the subject is adequately restrained to prevent any movement, a wand tool with RF transmitters can be used to point to fixed locations that are henceforth assumed to remain fixed.

Next, the position of the medical instrument itself is tracked. RF signals emitted from the RF transmitters (see FIG. 1 RF transmitter 120, RF tip 110) are received by RF receivers 130. The RF receivers 130 communicate said received RF signal to computer 210 through connection 205. Since computer 210 has calibrated the position of the anatomical representation and the position of each of the RF receivers 130 relative to each other (see FIG. 1 LPS 160), it is able to triangulate the precise position of the surgical instrument (see FIG. 1 instrument 150) and determine its position in relation to both the coordinate system of the room and the anatomical representation.

An anatomical representation is captured by a means for acquiring an anatomical image of the subject 230. In one embodiment of the present invention, the means for acquiring an anatomical image of the subject 230 is an x-ray. Alternatively, the means for acquiring an anatomical image of the subject 230 is a tomographic image. Other types of anatomical imaging methods also may be employed. The anatomical representation captured by the means for acquiring an anatomical image 230 is communicated to computer 210 through connection 215.

Computer 210 then superimposes the location of the medical instrument on the anatomical image sent by means for anatomical image 230. This superimposition is sent to display means 220 through connection 225, where it is displayed on display means 220. The user of the present invention can see precisely where surgical instrument (see FIG. 1 instrument 150) is located inside the body of the subject. According to an embodiment of the invention, the user of the present invention can make user inputs 240 in order to change options. For example, the user of the present invention may prefer to view a smaller portion of the anatomical image with the superimposed surgical device. The user of the present invention can input this preference through user input 240, and the display shown on display means 220 should react accordingly.

In another embodiment of the present invention, computer 210 is connected to a controller which is used to control a robotic apparatus (e.g., an end of arm tool on which a medical instrument can be mounted). Any data received or computed by computer 210 is available to the controller for controlling a robotic apparatus, and any information known by the controller is available to the computer 210. The controller can use this information to control the robotic apparatus for uses such as conducting or assisting in medical procedures. In one embodiment, the computer 210 sends the controller the location of the desired point of insertion and the coordinates of the target end point for the surgical instrument. Computer 210 also sends the controller the desired path of insertion. The controller signals the robotic apparatus to insert the needle at the desired location, follow the desired path and reach the target point. Concurrently, computer 210 dynamically and continuously sends the controller the location of the surgical device, while the controller sends computer 210 the location of the robotic apparatus. Computer 210 can compare the two locations along with the desired navigation path. If there is a discrepancy between the desired navigation path and the location of the robotic apparatus, then computer 210 can communicate to the controller to make corrective adjustments to the position of the robotic apparatus.

Figure 3:
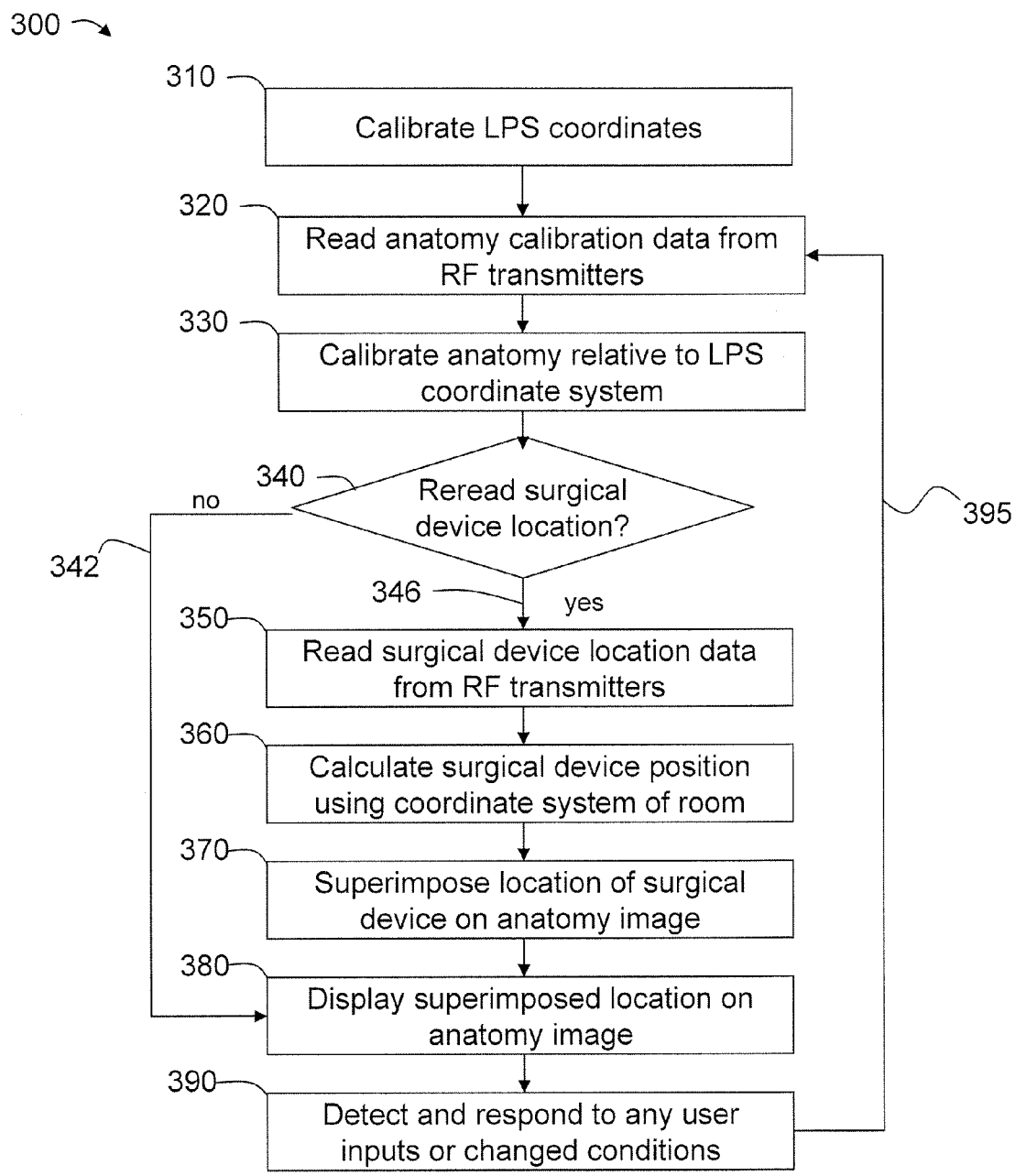
FIG. 3 is a flow diagram for the tracking of a medical device used in an invasive procedure according to an embodiment of the present invention.

FIG. 3 is a flow diagram for the tracking of a medical device used in an invasive procedure 300, according to an embodiment of the present invention.

First, at step 310, the LPS coordinate system of the operating room is calibrated. Next, at step 320, RF data for calibrating the anatomy is read. This RF data for calibrating the anatomy is transmitted by RF transmitters which can be attached to anatomical structures in known locations. Next, at step 330, the anatomy relative to the LPS coordinate system is calibrated.

At step 340, the user is asked whether the location of the surgical device should be reread. If the user chooses yes 346, then the surgical device location data transmitted from the RF transmitters on the surgical device is read in at step 350, and the position of the surgical device is calculated using the coordinate system of the room at step 360. Next, the location of the surgical device is superimposed on an image of the subject's anatomy at step 370, which is displayed to the user at step 380.

If at step 340 the user chooses not to update the location of the surgical device by answering no 342, then the display simply shows the last calculated image at step 380. If there was no previous image, then the display does not show anything.

Regardless of whether path 342 or 346 is taken, the next step after 380 is detecting and responding to any user inputs or changed conditions at step 390. For example, the user may want to change the anatomical area shown on the screen. Finally, the system loops back to step 320 through return loop 395.

In an alternative embodiment, step 390 includes detecting and responding to any user inputs or changed conditions relating to any use of the machine. For example, at step 390 the system could detect a user request to increase RF energy in the beveled tip (see FIG. 4).

In an alternative embodiment, step 390 includes a user-controlled option to change the RF energy in the tip of the surgical device from a level that is useful for tracking the position of the surgical device to a level for improving navigation of surgical device during insertion into the body.

In an alternative embodiment, the system automatically continuously updates the location of the surgical device without any affirmative user input to do so. The continuous dynamic feedback of the precise position of surgical instruments and/or medical apparatuses relative to the subject's anatomy allows dynamic correction for any deviation along the navigational path and/or any motion of the subject's body.

Currently, to determine the position of a surgical instrument that is internal to the body of the subject, to track the instrument's path relative to a navigation plan, and to efficiently arrive at the planned target is quite cumbersome.

An alternative embodiment of the invention includes a step that tracks and logs surgical instruments during surgical procedures, which improves the safety of surgical procedures. The Local Positioning System (LPS) in conjunction with the RF identifiers on surgical instruments allows the process of tracking and recording the RF identifiers to be fully automatic. The instrumentation will be tracked both by its position and its identity during the course of the surgical procedure. This allows medical staff to precisely reach a targeted position within the body, which improves the safety of surgical procedures and expands the use of minimally invasive surgery. Logging the RF identifiers will also help prevent instrumentation from being left inside the subject after the surgical procedure has been completed.

Figure 4:
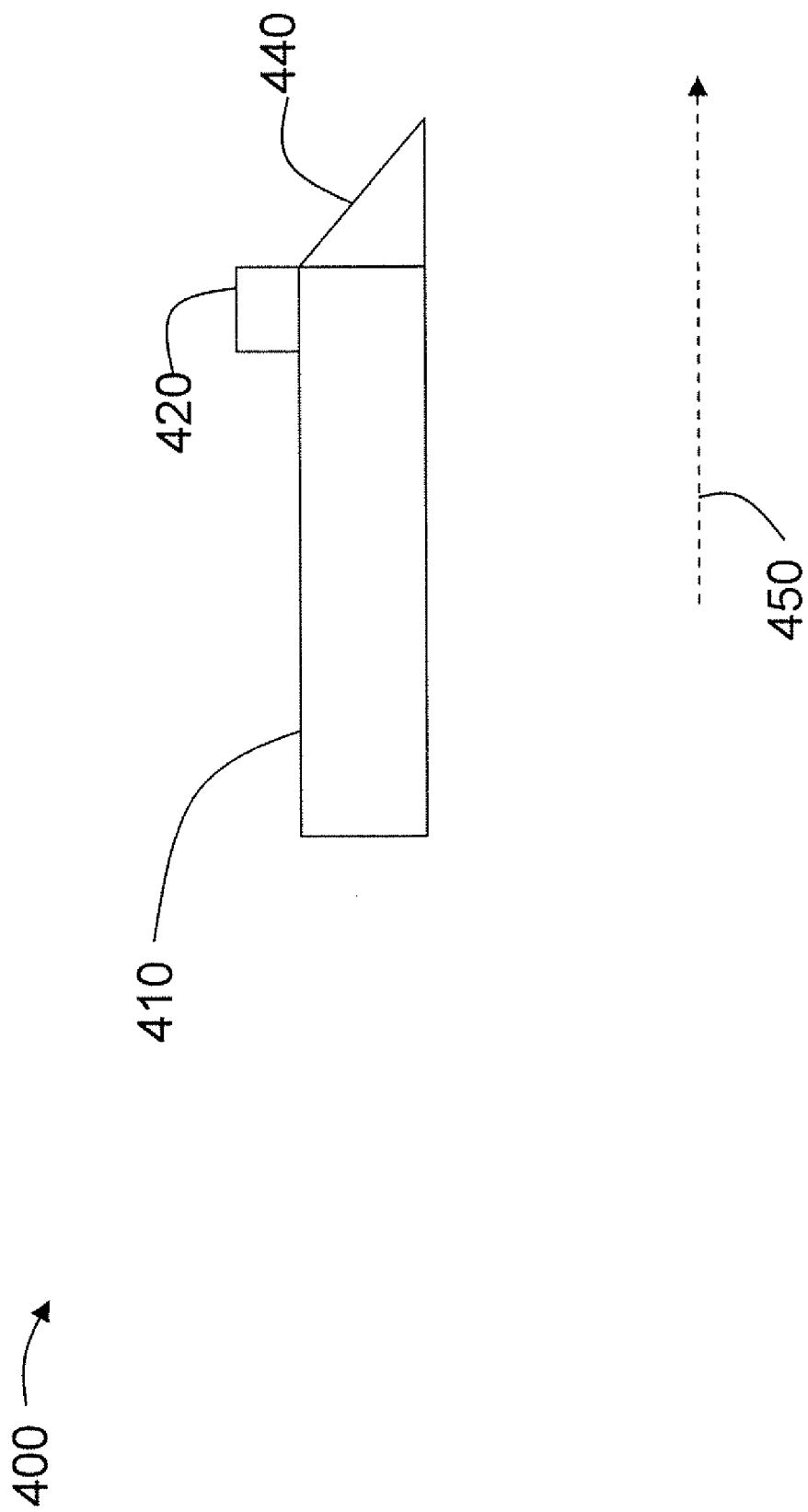
FIG. 4 is a schematic diagram of a detailed view of a surgical device for insertion into the body according to an embodiment of the invention.

FIG. 4 is a schematic diagram of a detailed view of a surgical device for insertion into the body 400, according to an embodiment of the invention. Surgical device 400 includes an injecting needle 410, which is for insertion into a body. Injecting needle 410 includes beveled tip 440 and electrode 420. Electrode 420 can be either attached or embedded to injecting needle 410. Insertion direction 450 illustrates which direction injection needle 410 is injected into the body.

Electrode 420 can either be a monopolar electrode (with a neutral electrode somewhere on the subject through which the energy dissipates) or one of two bipolar electrodes. If electrode 420 is a monopolar electrode, the beveled tip 440 would need to be made of metal and the rest of injecting needle 410 made of some insulating material to prevent the return of energy down the needle shaft. If electrode 420 is a bipolar electrode, beveled tip 440 would act as one electrode and the shaft of injecting needle 410 (or a portion of the shaft) as the other electrode. Injecting needle 410 and beveled tip 440 could be coaxial.

During operation, beveled tip 440 is energized by RF energy in electrode 420. Energizing beveled tip 440 allows easier penetration and reduces the amount of lateral deflection caused by the beveled tip.

The appropriate amount of energy (magnitude and waveform) needed to be applied to the beveled tip 440 is enough to allow the injecting needle 410 to penetrate easily through tissues but not destroy excessive amounts of tissue. Corrections and adjustments in energy level and waveform will be accomplished by a manual adjustment of the controller or automated based on sensing applied force, needle deflection and/or numerical modeling of tissue. Selectively activating the RF energy can be used to navigate the slender medical instrument through variations in tissues using manual or automated systems. One reference for selecting the appropriate energy level is the Ellman website disclosed above.

Alternatively, beveled tip 440 is energized to a level that is used for tracking injecting needle 410 as disclosed in FIG. 1. The switch between a level that is used for tracking injecting needle 410 and any other useful level of RF energy can be either user-initiated, automatic, or a combination of both.

In some cases, it may be desirable to use the bevel to the user's advantage. That is, since it is known that the bevel will force the beveled tip 440 laterally in a certain direction, and since it is known that energizing the tip will reduce the magnitude of the lateral deflection, these attributes can be used to steer the needle tip. By manually dialing up or down the amount of energy or automating the amount of energy in beveled tip 440, the user can control the tip to deflect by a range of possible amounts for sharp or gradual turns. Furthermore, the direction of the bevel could change easily by simply rotating the entire injecting needle 410, assuming the needle is sheathed loosely enough that it can rotate within the sheath.

In an alternative embodiment, there could be two electrodes at the tip—one on the bevel side and one on the flat side. By selectively activating one of the electrodes, it would either create a sharper turn than without energization (straight side activated) or a less of a turn than without energization (bevel side activated). These two electrodes could both act as monopolar electrodes, or they could be switched to act as two parts of a bipolar electrode if the difficulty of steering is not an issue.

In an alternative embodiment, the tip of a solid guide wire (not shown) is energized as opposed to using the bevel to achieve a controlled curved path. The guide wire would have a sharp conical tip instead of a flat beveled tip. After the guide wire is inserted to its destination (curved or straight path), a cannula could be slipped over the wire. Alternately, the sheath (cannula) could be already be around the wire and then the wire would be extracted, leaving the cannula in place, after inserting the device to the desired location. Once the wire is out of the sheath, the user has the same final result of a tube through which injection or biopsy can be performed. This type of device without an energized tip is already commonly used clinically.

Trajectories of curved paths are important not only for the application described using a nitinol needle, but also in a new application not to our knowledge previously described: in the use of permanently-bent (non-shape-memory alloy) needles for biopsy or injection. A permanently bent needle or guide wire is curved along its entire path and its insertion is controlled by a device that feeds the needle out of a curved casing in a specific trajectory and location (possibly via a surgical robot).

The pre-bent curved needles could be available in a variety of user-defined radii and with the development of software the curved path of the needle could be planned. An energized pre-bent curved needle allows for a predictable path through various tissues knowing the radius, insertion point, and insertion trajectory. Thus, such a system allows the surgeon to plan on a medical image of the desired tip location, entry point, and curved path and then to manually or automatically insert a needle according to this plan. To account for deflection of the shaft, numerical modeling of tissue penetration may be necessary to overcome the deviation of the needle path relative to the path expected through air. Selectively activating the RF energy at the tip of a needle or wire tip using a numerical model controls its penetration into the tissue and improves the accuracy of such a plan.

It should be noted that the radio frequency signal emitted by the tip of the needle or guide wire could be used for different purposes depending on the stage of the procedure. For example, low cutting energy without hemostasis could be applied during entry through the skin and superficial layers. After passing through these tissues, energy could be altered to cause hemostasis while the needle or wire passes through tissue that is sensitive to bleeding, such as the liver. Then, cutting energy could be increased further to pass through bone and cartilage. Further, if the terminal destination is a tumor, the tip could be highly energized to ablate the tumor. Note that this example uses several different waveforms/energy levels of the tip. Finally, the energy at the tip can be used for RF tracking as disclosed in FIGS. 1-3.

One exemplary embodiment of the present invention is a navigation system for invasive medical procedures. This navigation system includes a medical instrument that may be mounted on an end of arm tool and that is adapted to be inserted into a human body. A radio frequency (RF) transmitter is affixed to a distal end of the medical instrument. The system also includes a plurality of RF receivers that are adapted to receive RF signals emitted from the RF transmitter, as well as a computational device that is adapted to be operatively coupled to the plurality of RF receivers. The computational device is adapted to cause a visual image of a desired portion of a human body to be shown on a display and to overlay on the visual image an indication of the location of the medical instrument within the human body based on analysis of the information received from the RF receivers. A controller that is operatively coupled to the computational device and the end of arm tool is used to cause the end of arm tool to move the medical instrument to desired locations within a human body.

In one application, the medical instrument comprises a needle or has a beveled leading edge. The RF transmitter can be located on the distal end of the medical instrument so that RF energy can be emitted therefrom which produces a force that balances the mechanical displacement force created by the beveled edge of the medical instrument. Three or more RF receivers can be used.

The computational device is adapted to receive information from the RF receivers in an iterative fashion. Alternatively, the computational device is adapted to receive information from the RF receiver in a dynamic fashion.

In an exemplary embodiment, the computational device is adapted to allow a user to pick a desired location within a human body and to dynamically provide information to the controller to cause it to move the end of arm tool and medical instrument to the desired location. The computation device comprises a personal computer.

The RF transmitter can be located at a leading edge of the medical instrument. The RF transmitter is operatively coupled to the computational device, the computational device causing the RF transmitter to emit RF signals at desired times.

If desired, two or more RF transmitters can be affixed to the medical instrument at certain locations thereof, the two or more RF transmitters being selectively energizable to generate forces that are applied to the medical instrument and cause at least a portion of it to move in a desired direction. Similarly, at least three RF transmitters can be affixed to the medical instrument at desired locations thereof, if desired, the three RF transmitters being selectively energizable to generate forces that are applied to the medical instrument cause at least a portion of it to move in a desired direction. The three RF transmitters can be evenly radially distributed around the medical instrument, at a distal end of the medical instrument and/or on a leading edge of the medical instrument.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed:

1. A navigation system for invasive medical procedures, comprising:
   an RF steerable medical instrument that is mounted on an end of arm tool, the medical instrument being adapted to be inserted into a human body along an axis of insertion;
   at least one radio frequency (RF) transmitter affixed to a distal end and on a side of the medical instrument, said RF transmitter capable of emitting energy sufficient to ablate abutting tissue;
   a plurality of RF receivers that are adapted to receive RF signals emitted from the RF transmitter;
   a computational device that is operatively coupled to the plurality of RF receivers, the computational device being adapted to cause a visual image of a desired portion of a human body to be shown on a display and to overlay on the visual image an indication of the location of the medical instrument within the human body based on analysis of the information received from the RF receivers; and a robotic controller that is operatively coupled to the computational device and the end of arm tool, the controller configured to steer the medical instrument to desired locations within a human body by selectively activating the RF transmitter to emit energy in an amount sufficient to control the degree of deflection of the medical instrument lateral to the axis of insertion.

2. The system of claim 1, wherein the medical instrument comprises a needle.

3. The system of claim 1, wherein the medical instrument includes a beveled leading edge, the RF transmitter being located on the distal end of the medical instrument so that RF energy can be emitted therefrom which reduces a mechanical force needed to advance the medical instrument through tissue opposing the beveled edge of the medical instrument.

4. The system of claim 1, wherein the plurality of RF receivers comprises three or more RF receivers.

5. The system of claim 1, wherein the computational device is adapted to receive information from the RF receivers in an iterative fashion.

6. The system of claim 1, wherein the computational device is adapted to receive information from the RF receiver in a dynamic fashion.

7. The system of claim 1, wherein the computational device is adapted to allow a user to pick a desired location within a human body and to dynamically provide information to the controller to cause it to move the end of arm tool and medical instrument to the desired location.

8. The system of claim 1, wherein the computation device comprises a personal computer.

9. The system of claim 1, wherein the RF transmitter is located at a leading edge of the medical instrument.

10. The system of claim 1, wherein the RF transmitter is operatively coupled to the computational device, and wherein the computational device causes the RF transmitter to emit RF signals at desired times.

11. The system of claim 1, wherein two or more RF transmitters are affixed to the medical instrument at desired locations thereof, the two or more RF transmitters being selectively energizable to steer the medical instrument in a desired direction.

12. The system of claim 1, wherein at least three RF transmitters are affixed to the medical instrument at desired locations thereof, the three RF transmitters being selectively energizable to steer the medical instrument in a desired direction.

13. The system of claim 12, wherein the three RF transmitters are evenly radially distributed around the medical instrument.

14. The system of claim 13, wherein the three RF transmitters are located at a distal end of the medical instrument.

15. The system of claim 14, wherein at least one of the three RF transmitters are located opposite a leading edge of the medical instrument.

* * * * *